United States Patent
Barreira et al.

(10) Patent No.: US 11,071,699 B2
(45) Date of Patent: Jul. 27, 2021

(54) DEODORANT COMPOSITION

(71) Applicant: CONOPCO, INC., Englewood Cliffs, NJ (US)

(72) Inventors: Raquel Alzira Cunha Barreira, Trumbull, CT (US); David Allen Brewster, Trumbull, CT (US); Elodie Aurore Suzanne Deguerville, Leeds (GB); Bruce Steven Emslie, Leeds (GB); Alyssa Victoria Kowcz, Trumbull, CT (US)

(73) Assignee: Conopco, Inc, Englewood Cliffs, NJ (US)

( * ) Notice: Subject to any disclaimer, the term of this patent is extended or adjusted under 35 U.S.C. 154(b) by 380 days.

(21) Appl. No.: 16/092,425

(22) PCT Filed: Apr. 12, 2017

(86) PCT No.: PCT/EP2017/058766
§ 371 (c)(1),
(2) Date: Oct. 9, 2018

(87) PCT Pub. No.: WO2017/182358
PCT Pub. Date: Oct. 26, 2017

(65) Prior Publication Data
US 2020/0323754 A1 Oct. 15, 2020

(30) Foreign Application Priority Data
Apr. 19, 2016 (EP) ..................... 16166000

(51) Int. Cl.
A61K 8/34 (2006.01)
A61K 8/02 (2006.01)
A61K 8/36 (2006.01)
A61Q 15/00 (2006.01)

(52) U.S. Cl.
CPC ............ *A61K 8/345* (2013.01); *A61K 8/0229* (2013.01); *A61K 8/361* (2013.01); *A61Q 15/00* (2013.01)

(58) Field of Classification Search
None
See application file for complete search history.

(56) References Cited

U.S. PATENT DOCUMENTS

| 5,543,148 A | 8/1996 | Lapidus |
| 5,650,142 A | 7/1997 | Bergmann et al. |
| 5,863,524 A | 1/1999 | Mason et al. |
| 6,001,341 A | 12/1999 | Genova et al. |
| 6,165,480 A | 12/2000 | Kasat et al. |
| 2004/0258721 A1 | 12/2004 | Bauer et al. |
| 2005/0048013 A1 | 3/2005 | Diec et al. |
| 2006/0029624 A1 | 2/2006 | Banowski et al. |
| 2010/0047296 A1 | 2/2010 | Banowski et al. |
| 2010/0158841 A1 | 6/2010 | Brewster |
| 2011/0300091 A1 | 12/2011 | Demson et al. |

FOREIGN PATENT DOCUMENTS

| EP | 0386900 | 9/1990 |
| EP | 0521579 | 1/1993 |
| EP | 0714655 | 6/1996 |
| EP | 1310234 | 5/2003 |
| EP | 2465487 | 6/2012 |
| FR | 2823504 | 10/2002 |
| GB | 1442426 | 7/1976 |
| KR | 100789345 | 12/2007 |
| WO | WO9407459 | 4/1994 |
| WO | WO9632091 | 10/1996 |
| WO | WO9703636 | 2/1997 |
| WO | WO9709959 | 3/1997 |
| WO | WO9745093 | 12/1997 |
| WO | WO03030854 | 4/2003 |
| WO | WO2006119981 | 11/2006 |
| WO | WO2006136330 | 12/2006 |
| WO | WO2009046008 | 4/2009 |

OTHER PUBLICATIONS

Search Report & Written Opinion in EP16166000; dated Oct. 7, 2016.
Search Report and Written Opinion in PCTEP2017058766; dated Jun. 12, 2017.

*Primary Examiner* — Jessica Worsham
(74) *Attorney, Agent, or Firm* — Foley & Lardner LLP

(57) ABSTRACT

The invention relates to a deodorant composition in the form of a solid stick comprising: a) from 24 to 55 wt. % of dipropylene glycol; b) from 4 to 8 wt. % of propylene glycol; c) from 10 to 20 wt. % of glycerol; d) from 20 to 40 wt. % of water; and, e) from 0.5 to 15 wt. % of a structurant; wherein, the weight ratio of dipropylene glycol (a), to propylene glycol (b) is greater than 5:1; and, wherein, the weight ratio of dipropylene glycol (a), to glycerol (c) is from 1:1 to 3:1.

19 Claims, No Drawings

DEODORANT COMPOSITION

CROSS REFERENCE TO RELATED APPLICATIONS

The present application is a U.S. National Phase Application under 35 U.S.C. § 371 of International Application No. PCT/EP2017/058766, filed on Apr. 12, 2017, which claims priority to European patent application No. 16166000.6 filed on Apr. 19, 2016, the contents of which are incorporated herein in their entireties.

FIELD OF THE INVENTION

The invention relates to a deodorant composition, more particularly it relates to a deodorant composition in the form of a stick.

BACKGROUND OF THE INVENTION

Deodorant and antiperspirant products are designed to control sweating or to control the odour associated with sweating. While some formulations will include a specific active such as an aluminium active, other formulations may be aluminium free. The formulation is usually dispensed from a package suitable for application to the consumer's body, usually to the underarm area. The product of the invention is related to a formulation dispensed in the form of a stick that contains a formulation based on dipropylene glycol, propylene glycol, and water.

US 2011/300091 discloses a stick that includes as a solvent a glycol or a mixture of glycols. The preferred stick uses a ratio of dipropylene glycol to propylene glycol at a weight ratio close to 1:1.

US 2010/0158841 discloses a clear stick that includes dipropylene glycol to propylene glycol at a weight ratio of 1.78:1.

U.S. Pat. No. 5,863,524 discloses a stick comprising a polyhydric alcohol. A preferred polyhydric alcohol mixture is predominantly propylene glycol with a minor amount of dipropylene glycol.

It is desired to add humectant materials to provide moisturisation to the underarm area. A useful humectant ingredient is glycerol.

SUMMARY OF THE INVENTION

There is a problem that inclusion of glycerol into some stick formulations comprising a combination of dipropylene glycol, propylene glycol with water leads to formulations that are not stable due to sweating of the stick.

It is also a problem that in factories that manufacture both aluminium and non-aluminium deodorant/antiperspirant sticks that some aluminium contamination is inevitable. This can cause insoluble matter such as white specs to appear in non-aluminium formulations.

It is an object of the invention to improve the characteristics of the stick, in terms of the sweating of the stick and to reduce or eliminate any insoluble matter such as white specs in the stick.

We have now found that using a specific combination of ingredients, in specific weight ratios, that both the sweating of the stick, and the level of the insoluble matter present in the stick are reduced.

There is provided in a first aspect of the invention, a deodorant composition in the form of a solid stick comprising:— a) from 24 to 55 wt. % of dipropylene glycol;
b) from 4 to 8 wt. % of propylene glycol;
c) from 10 to 20 wt. % of glycerol;
d) from 20 to 40 wt. % of water; and,
e) from 0.5 to 15 wt. % of a structurant wherein, the wherein the weight ratio of dipropylene glycol (a), to propylene glycol (b) is greater than 5:1; and, wherein, the weight ratio of dipropylene glycol (a), to glycerol (c) is from 1:1 to 3:1.

A second aspect of the invention provides a stick product comprising the composition of the first aspect comprised within a stick dispenser product package.

DETAILED DESCRIPTION OF THE INVENTION

The composition comprises dipropylene glycol at a level of from 24 to 55 wt. %, preferably from 36 to 44 wt. %.

The composition comprises propylene glycol. Propylene glycol is present at a level of from 4 to 8 wt. %, preferably from 5 to 6.25 wt. %.

The composition comprises glycerol at a level of from 10 to 20 wt. %, preferably from 15 to 20 wt. %.

The composition may optionally comprise an emollient or one or more further humectants to aid the sensory profile. If present, then this optional material is preferably included at a level of from 0.5 to 20 wt. %, preferably from 1 to 10 wt. %. These values do not include any glycerol (which is a humectant) already included in the formulation.

The composition comprises water in the composition. Water is present at a level of from 20 to 40 wt. %, preferably from 22 to 36 wt. %, more preferably from 24 to 32 wt. %.

The weight ratio of dipropylene glycol (a), to propylene glycol (b) is greater than 5:1. Preferably, the weight ratio of dipropylene glycol (a), to propylene glycol (b) is from 5.5:1 to 10:1, more preferably from 6:1 to 10:1, even more preferably from 7:1 to 10:1.

This weight ratio of dipropylene glycol to propylene glycol is believed to be critical to reduce the sweating of the stick as well as reducing or eliminating any insoluble matter in the composition.

The weight ratio of dipropylene glycol (a), to glycerol (c) is from 1:1 to 3:1, preferably from 1.5:1 to 2.75:1, more preferably from 2:1 to 2.5:1.

The composition comprises from 0.5 to 15 wt. % of a structurant. This may be a single structurant or a mixture of structurants. Preferably, the composition comprises from 1 to 8 wt. %, preferably from 2 to 6 wt. % of a structurant.

Preferably the structurant is 1 to 8 wt. %, more preferably 2 to 6 wt. % of a 012 to 024 fatty acid or salt thereof. Most preferably the fatty acid or salt thereof is sodium stearate.

A co-structurant can be used. An example of a co-structurant includes nonionic surfactants such as polymeric nonionic surfactants for example poloxamine (Tetronic® 1307).

Preferably, the composition comprises from 0.1 to 2 wt. % of a perfume.

A preferred composition is a deodorant composition in the form of a solid stick comprising:— a) from 36 to 44 wt. % of dipropylene glycol;
b) from 5 to 6.25 wt. % of propylene glycol;
c) from 15 to 20 wt. % of glycerol;
d) from 24 to 32 wt. % of water;
e) from 2 to 6 wt. % of sodium stearate; and,
f) from 0.1 to 2 wt. % of a perfume;

wherein, the wherein the weight ratio of dipropylene glycol (a), to propylene glycol (b) is from 7:1 to 10:1; and, wherein, the weight ratio of dipropylene glycol (a), to glycerol (c) is from 1:1 to 3:1.

The personal care product is in the form of a stick; preferably comprising the composition as hereinbefore described comprised within a stick dispenser product package.

Usual stick products are packaged so that there is a plastic dome on top of the stick, between the solid stick formulation and the cap. The dome is removed and discarded by the consumer prior to first use. There is also provided a cap which can be replaced after each use.

The composition may comprise one or more of any of the following additional optional ingredients such as: dyes, pigments or colourants; antioxidants such as butylated hydroxytoluene (BHT); surfactants, including nonionic surfactants, such as polymer based nonionic surfactants, for example poloxamine (Tetronic® 1307); chelating agents such as disodium EDTA; deodorising agents; silicones; and, antifoam agents, for example silicone/hydrated silica antifoam agents.

Without wishing to be bound by theory, we believe that the insoluble matter, usually manifesting as white specs in the stick are caused by small levels of aluminium contaminants, which may be present in salt form, due the factories being used to process multiple formulations, both aluminium and non-aluminium. The aluminium salt contaminants would be for example aluminium salts of structurants such as stearate, e.g. aluminium stearate.

EXAMPLES

Example 1—Stick Appearance

Various carrier materials/solvents that were possibilities to be used in stick formulations were tested for the presence of insoluble matter such as white specs.

Example carrier solvents for the sticks were prepared comprising propylene glycol, dipropylene glycol and glycerol in various amounts. They are listed in table 1. Compositions with numbers are according to the invention, those with letters are comparative. Numbers are listed as parts by weight of the test formulation. To test whether these carrier solvents will solubilise aluminium salts, we used a test aluminium salt, namely aluminium stearate. To the test formulations in table 1, aluminium stearate (0.01%) was added, and the test formulation was left to see if the resulting mixture had any insoluble matter present.

The formulations with the levels of DPG, PG and glycerol (in parts by weight), listed in table 1 were made and analysed for the presence of insoluble matter (white specs). They were graded for presence of insoluble matter (white specs) as follows:—none present, some white specs present or many white specs present.

TABLE 1

|  | 1 | 2 | A | B | C | D | E | F | G |
|---|---|---|---|---|---|---|---|---|---|
| Dipropylene Glycol | 40 | 41.29 | 34.3 | 40 | 29.8 | 40 | 34.65 | 44.1 | 25.2 |
| Propylene Glycol | 5.5 | 5.71 | 19.7 | 22.5 | 15.2 | 14.5 | 10.71 | 9.45 | 31.5 |
| Glycerol | 18 | 17 | 9 | 1 | 18 | 9 | 17.64 | 9.45 | 6.3 |
| Weight ratio of DPG:PG | 7.27:1 | 7.23:1 | 1.74:1 | 1.78:1 | 1.96:1 | 2.75:1 | 3.24:1 | 4.67:1 | 1:1.25 |
| Weight ratio of DPG:Glycerol | 2.22:1 | 2.43:1 | 3.81:1 | 40:1 | 1.66:1 | 4.45:1 | 1.96:1 | 4.67:1 | 4:1 |
| Insoluble matter (white specs) present? | None | None | Many | Some | Many | Some | Many | Some | Many |

It is clear from table 1, that only when the weight ratio of DPG:PG is >5:1, or even better >7:1, that the presence of insoluble matter is minimised.

Example 2—Stick Stability (Stick Sweating Characteristics)

Sticks were manufactured in accordance with the formulations in Table 2.

The processing instructions were as follows:—

Add the EDTA and water to a beaker and heat to 50° C. to dissolve.

Once EDTA has dissolved, add Glycerol, DPG, PG, Simethicone and BHT to beaker.

Mix beaker contents while heating to 85° C.

At 85° C. add the sodium stearate, mix until dissolved. Mix for 5 mins then add the Poloxamine copolymer surfactant.

Continue mixing for 5 minutes then start cooling to 74° C.

At 74° C. add the dye solution and then fragrance, if required, and mix for 5 minutes.

Continue stirring/cooling to 72° C.

Pour into barrels at 72° C. to finalise the stick product.

The sticks were subsequently kept at −4° C. for 3 days, then allowed to return to room temperature for 24 hours followed by assessment for sweating behaviour. This was done in various ways, with the dome and cap on, dome on and cap off and with both dome and cap off. The level of droplets that have leaked from the formulation was assessed, mainly on the product packaging, usually the dome and cap.

TABLE 2

|  | 1 | H | I |
|---|---|---|---|
| Dipropylene Glycol | 40.00 | 40.00 | 29.80 |
| Propylene Glycol | 5.50 | 22.50 | 15.20 |
| Glycerol | 17.00 | — | 17.00 |
| Water | 27.73 | 26.34 | 29.73 |
| Sodium stearate | 5.50 | 5.50 | 6.00 |
| Copolymer Surfactant (Tetronic 1307) | 2.00 | 3.00 | — |
| Disodium EDTA | 0.10 | 0.10 | 0.10 |

TABLE 2-continued

|  | 1 | H | I |
|---|---|---|---|
| BHT | 0.05 | 0.05 | 0.05 |
| Aminomethyl propanol-95 | — | 0.40 | — |
| Dye | 1.00 | 1.00 | 1.00 |
| Simethicone | 0.02 | 0.02 | 0.02 |
| Fragrance | 1.10 | 1.10 | 1.10 |
| Weight ratio of DPG:PG | 7.27:1 | 1.78:1 | 1.96:1 |

The level of sweating was assessed to be:—H>I>>1

This shows that the composition according to the invention displayed less sweating than for either of the comparative examples.

The invention claimed is:

1. A deodorant composition in the form of a solid stick comprising:
   a) from 24 to 55 wt. % of dipropylene glycol;
   b) from 4 to 8 wt. % of propylene glycol;
   c) from 10 to 20 wt. % of glycerol;
   d) from 20 to 40 wt. % of water; and,
   e) from 0.5 to 15 wt. % of a structurant;
   wherein, the weight ratio of dipropylene glycol to propylene glycol is greater than 5:1; and,
   wherein, the weight ratio of dipropylene glycol to glycerol is from 1:1 to 3:1.

2. The composition of claim 1, wherein the wt. % of dipropylene glycol is from 36 to 44 wt. %.

3. The composition of claim 1, wherein the wt. % of propylene glycol is from 5 to 6.25 wt. %.

4. The composition of claim 1, wherein the wt. % of glycerol is from 15 to 20 wt. %.

5. The composition of claim 1, wherein the wt. % of water is from 22 to 36 wt. %.

6. The composition of claim 1, wherein the weight ratio of dipropylene glycol to propylene glycol is from 5.5:1 to 10:1.

7. The composition of claim 1, wherein the weight ratio of dipropylene glycol to glycerol is from 1.5:1 to 2.75:1.

8. The composition of claim 1, wherein the structurant is present at a level of from 1 to 8 wt. %.

9. The composition of claim, 1 wherein the structurant is a $C_{12}$ to $C_{24}$ fatty acid or salt thereof.

10. The composition of claim 9, wherein the fatty acid or salt thereof is sodium stearate.

11. The composition of claim 1, further comprising from 0.1 to 2 wt. % of a perfume.

12. A deodorant composition in the form of a stick comprising:
   a) from 36 to 44 wt. % of dipropylene glycol;
   b) from 5 to 6.25 wt. % of propylene glycol;
   c) from 15 to 20 wt. % of glycerol;
   d) from 24 to 32 wt. % of water;
   e) from 2 to 6 wt. % of sodium stearate; and,
   f) from 0.1 to 2 wt. % of a perfume;
   wherein the weight ratio of dipropylene glycol to propylene glycol is from 7:1 to 10:1; and,
   wherein, the weight ratio of dipropylene glycol to glycerol is from 1:1 to 3:1.

13. A personal care product in the form of a stick, comprising the deodorant composition of claim 1, wherein the composition is contained within a stick dispenser product package.

14. A personal care product in the form of a stick, comprising the deodorant composition of claim 12, wherein the composition is contained within a stick dispenser product package.

15. The composition of claim 1, wherein the wt. % of water is from 24 to 32 wt. %.

16. The composition of claim 1, wherein the weight ratio of dipropylene glycol to propylene glycol is from 6:1 to 10:1.

17. The composition of claim 1, wherein the weight ratio of dipropylene glycol to propylene glycol is from 7:1 to 10:1.

18. The composition of claim 1, wherein the weight ratio of dipropylene glycol to glycerol is from 2:1 to 2.5:1.

19. The composition of claim 1, wherein the structurant is present at a level of from 2 to 6 wt. %.

* * * * *